April 18, 1972 H. A. JOHNSON, JR., ET AL Plant Pat. 3,123
STRAWBERRY PLANT
Filed April 17, 1970
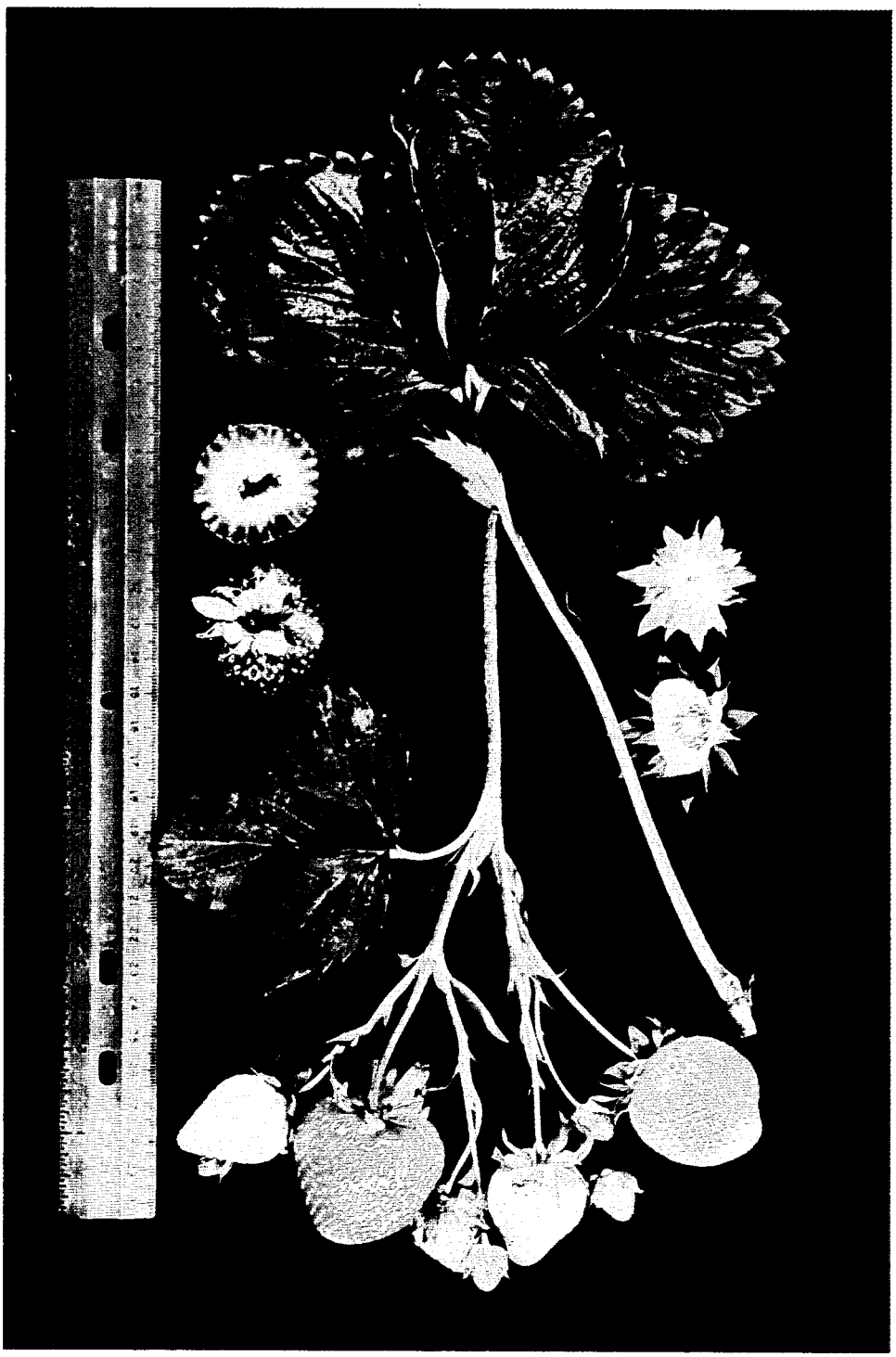
Townsend and Townsend
ATTORNEYS
INVENTORS
HAROLD A. JOHNSON JR.
HAROLD E. THOMAS United States Patent Office Plant Pat. 3,123
Patented Apr. 18, 1972

3,123
STRAWBERRY PLANT

Harold A. Johnson, Jr., and Harold E. Thomas, Watsonville, Calif., assignors to Driscoll Strawberry Associates, Inc., Watsonville, Calif.

Filed Apr. 17, 1970, Ser. No. 29,712
Int. Cl. A01h 5/03
U.S. Cl. Plt.—49 1 Claim This invention relates to a new and distinct variety of strawberry plant which is the result of a cross of the patented everbearing variety known to The Strawberry Institute of California as Selection E3, Patent No. 2,891, and The Strawberry Institute of California Selection NM55.5.

The seedlings resulting from the aforementioned cross were grown and asexually multiplied in Shasta County, Calif., and tested in the fruiting beds on the property of growers of the Driscoll Strawberry Associates, Inc. Clones of the seedlings were also held at the Propagation Nursery in Shasta County. One plant was selected from the aforementioned group of seedlings and further asexually reproduced in the Shasta County nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

Plant parts of the new variety, typical in size, shape and color are pictured in the accompanying photograph. A berry in cross section illustrates flesh color and characteristic core cavity. The inflorescence pictured illustrates typical branching and relative size about the middle of July. The picture shows the presence of two secondary peduncles, but often there are three or four present on a single inflorescence. It is not uncommon to find a compound inflorescence where two distinct inflorescences branch from a single common peduncle. The leaf shown is typical in appearance and size and the flower is also typical of primary and secondary flowers during this period of the year.

The novel plant is medium to large in size and vigorous. The transplant is comparatively large as it comes from the nursery and produces a vigorous young plant early in the spring with a strong crown crop generally resulting. It is a spring variety, but has the ability of uniform production during the first year after being planted unless the transplant receives an excess of chilling before being planted, or if chilling temperatures are too excessive after being planted. The primary berries from the crown crop and the main crop are large and showy with an excellent gloss. Subsequent crops have fruit that is smaller in size, but consistently acceptable fruit for commercial fresh market distribution is usually maintained. The crown crop may commence during the latter part of April with the main crop starting the last of May in first year winter plantings. The crop is continuous and uniform in production from this spring period through the summer and fall. The crop during the second fruiting year as well as the spring crop from summer set plants starts fruiting in early to mid-May, with uniform production that continues throughout the late spring, summer, and fall periods.

This novel plant of the present invention is distinguished from other varieties by its flowers, fruit and plant characteristics. With proper chilling before being planted, the plant is vigorous enough to support a large crop the first year after a winter planting. Production is excellent during the second fruiting year, especially after an abundance of chilling received during the previous winter. The plant of this new variety is generally larger than the Goldsmith variety, Plant Patent No. 1,735. The leaflet size is generally equal to or larger than the Goldsmith, especially late in the fall when the leaflet size of the new variety remains large.

The plant color is generally lighter than the Goldsmith, especially during the late summer and fall period when it has a distinct pale color resulting in a chlorotic appearance. This light colored foliage gives the variety a distinct characteristic. The leaflets are less rugose than Goldsmith and have margins with larger and deeper serrations. Leaflets are positioned such that they are often parallel with the soil surface or cupped slightly downward in contrast to the Goldsmith variety whose leaflets are often directed upward. If this new variety receives an abundance of chilling during winter months after a winter planting, multiple crowns are produced along with a large plant, but not an abundance of runners as would the Goldsmith variety. While the individual crown size is larger than Goldsmith, the novel variety produces less runners at the nursery. Petioles of the new variety are generally longer than Goldsmith and have bracts in contrast to Goldsmith.

The inflorescence of this new variety is long, but usually not longer than Goldsmith. Generally, this new variety produces a long primary peduncle with short secondary peduncles and pedicels as illustrated in the accompanying picture. Many inflorescences produce a trifoliate leaf along with bracts at the axil of the peduncles. The pedicel holding the primary berry generally originates from the axil formed by secondary peduncles. Occasionally the pedicel holding the primary berry of any inflorescence originates from a peduncle, but if this is the case it generally joins the peduncle near the axil. Goldsmith produces shorter primary peduncles, but longer secondary peduncles and pedicels with the pedicel holding the primary berry originating from one of the secondary peduncles more often than does the new variety. It is not uncommon for the new variety to produce a compound inflorescence which is composed of two distinct inflorescences joined together on a peduncle near the crown. This compound fruiting spur or inflorescence does not produce a pedicel with a primary berry, but each inflorescence of the compound inflorescence or fruiting spur does have a primary berry. The inflorescence of this new variety is also peculiar in that it produces two or three ripe berries on the inflorescence at the same time.

Secondary berries often ripen at the same time as primaries and may be equal in size. During the spring period the flowers are visible above the plant, but during much of the remaining part of the year the flowers are located only below the top of the plant. The fruit produced from this novel variety is quite distinct in that the fruit surface is generally uniformly smooth with a high gloss. Seeds are uniformly distributed on the fruit surface and are usually slightly exerted. A distinctive characteristic of this variety is the apex of the fruit which often becomes lighter in color and may become seedy. Ridges and folded furrows are rare in this variety in contrast to Goldsmith which does not have the uniformly smooth surface or completely fertilized seed that the new variety possesses.

The shape of the new variety is mostly medium to long conic to medium wedge in outline, as described in the U.S.D.A. Bulletin No. 1,043. It is quite common for even the wedged shaped berries to produce one or two tips at the end of the fruit that may become seedy at the apex. This seediness is generally not abundant enough to deter from the fruit appearance, but it is a distinct character. The seeds are large and remain yellow on most of the fruit surface in contrast to the Goldsmith variety. Seed may become somewhat darker if the fruit is exposed to direct sunlight. The flesh and epidermis of this new variety is firm, making the variety valuable for interstate shipments. The fruit color of this new variety generally does not become dark or dull red, but remains glossy.

There are periods, however, when streaks of dark red show on individual berries.

The dessert quality of this new variety is good and is sweeter to the taste than the Goldsmith variety. There is generally a pleasant strawberry aroma peculiar to the flesh of this variety that may be more noticeable than in the Goldsmith variety.

Individual flowers are large and showy with more petals per flower than has the Goldsmith variety. The calyx of this variety is considered large, even larger than Goldsmith in proportion to the fruit size. Individual sepals of primary and secondary berries overlap considerably but vary in shape with an abundance of serrations.

This new variety appears to be more tolerant to the two-spotted mite than the Goldsmith variety, but is susceptible to mildew. It has not been completely tested against the Verticillium or Red Stele diseases. As a seedling and selection, this variety withstood the natural invasions of certain virus components found in central California without losing its ability to produce.

The varietal characteristics of the novel plant, described below in detail, were observed mainly during the first fruiting season, but reference is also made to the appearance during the second fruiting year. Observations were made in the Watsonville area of California which is a cool coastal area near the Pacific Ocean. The color terminology is in accordance with Ridgeways Color Standards and Nomenclature (1912 edition).

*Plants.*—Medium to large, vigorous is given ample chilling before being planted, and has an extensive root system.

*Leaves.*—Medium to large in size. The central leaflet is usually 6 to 9 cm. wide with the length being only slightly greater than the width. Petioles vary in length, but are usually 20 to 25 cm. from their base to the petiolules. Petiolules may be up to 10 mm. in length during the fall producing period. Bracts are generally present on the petiole. The leaflet serrations are deep and acute at the apex. The color of the upper side of the leaflet at Watsonville in July is Dark Dull Yellow Green, Plate XXXII.

*Runners.*—Runners are vigorous, but only medium in abundance both at the nursery and in the fruiting beds.

*Inflorescence.*—The inflorescence is 20 to 30 cm. long, depending on the time of year. The main common peduncle is generally long with short secondary peduncles and short pedicels. Secondary peduncles vary from 2 to 4 in number. Primary and secondary berries often ripen at the same time. Secondary berries may be as large or larger than primaries. The occurrence of two independent inflorescences having their main peduncles join at a primary peduncle at or near the crown is not uncommon. Hair on pedicels 20 mm. below tertiary flowers lies against and parallel with the pedicel. Pedicels holding primary berries usually originate at the axil formed by the union of peduncles, but it may originate from one of the peduncles at a point near the axil. Flowers are large and may be visible above the plant during spring and early summer periods. Many flowers average over 7 petals per flower. Another produces an abundance of pollen except during the early spring period on plants planted the previous summer.

*Fruit.*—Crown crop berries are generally large and of high quality, as well as the berries from the main first crop. Subsequent crop fruit size is medium to large with secondaries often equaling primaries. Primaries mainly 40 to 45 mm. in length with the width being slightly less. Production is comparatively uniform both first and second year during spring, summer and fall crops. Fruit shape is mainly medium to long conic to medium wedge. Shoulders are rounded at the calyx end and not necked. The fruit apex has a distinct light colored tip that may become seedy. Tips may be present even on wedge shaped fruit. Skin and flesh are firm with a small to medium core cavity. The fruit surface of primaries, secondaries and tertiaries is firm and smooth with a high gloss and have a uniform spacing of the seed. The seed is generally medium large and partially exerted. Seed generally remains yellow, but will darken to a limited degree when exposed to direct sunlight. The berry has a high dessert quality. The fruit surface color is Nople Red, Plate I, and the flesh color near the fruit surface is Scarlet, Plate I.

*Calyx.*—Large in diameter with primaries during July averaging 49 mm. in diameter. The calyx of small fruit is large in relation to fruit size. Sepals mostly overlap and are abundant. Sepals are elliptical ovate, or obovate and may possess serrations. The calyx is held free of the fruit surface and may become reflexed. Color of sepals on side facing the fruit is Varley's Green, Plate No. XVIII.

We claim:

1. The new and distinct variety of strawberry plant herein described and illustrated, and identified by the characteristics enumerated above.

No references cited.

ROBERT E. BAGWILL, Primary Examiner